United States Patent
Tuma et al.

(10) Patent No.: US 8,463,004 B2
(45) Date of Patent: Jun. 11, 2013

(54) DETERMINING SHAFT AND FEMUR NECK AXES AND THREE-DIMENSIONAL RECONSTRUCTION

(75) Inventors: Gregor Tuma, Munich (DE); Mario Schubert, Poing (DE); Frank Gruenschlaeger, Feldkirchen (DE); Martin Haimerl, Gilching (DE)

(73) Assignee: Brainlab AG, Feldkirchen (DE)

( * ) Notice: Subject to any disclaimer, the term of this patent is extended or adjusted under 35 U.S.C. 154(b) by 1924 days.

(21) Appl. No.: 11/356,737

(22) Filed: Feb. 17, 2006

(65) Prior Publication Data

US 2006/0204067 A1    Sep. 14, 2006

Related U.S. Application Data

(60) Provisional application No. 60/656,953, filed on Feb. 28, 2005.

(30) Foreign Application Priority Data

Feb. 18, 2005   (EP) .................................... 05003534

(51) Int. Cl.
  *G06K 9/00*   (2006.01)
(52) U.S. Cl.
  USPC .......................................... 382/128; 600/436
(58) Field of Classification Search
  USPC .......................................... 382/128; 600/436
  See application file for complete search history.

(56) References Cited

U.S. PATENT DOCUMENTS

| | | | |
|---|---|---|---|
| 6,701,174 B1 * | 3/2004 | Krause et al. | 600/407 |
| 6,711,432 B1 * | 3/2004 | Krause et al. | 600/427 |
| 2003/0176860 A1 * | 9/2003 | Shimura | 606/53 |
| 2006/0002632 A1 * | 1/2006 | Fu et al. | 382/294 |

FOREIGN PATENT DOCUMENTS

| | | |
|---|---|---|
| EP | 1 348 393 A1 | 10/2003 |
| EP | 1 348 394 A1 | 10/2003 |
| EP | 1 498 851 A1 | 1/2005 |
| WO | 01/22368 A1 | 3/2001 |

OTHER PUBLICATIONS

Hemant. "Deformable 2-D Template Matching Using Orthogonal Curves", IEEE transactions on medical imaging. Feb. 1997. 108-117.*

(Continued)

*Primary Examiner* — Max Hindenburg
*Assistant Examiner* — Renee Danega
(74) *Attorney, Agent, or Firm* — Renner, Otto, Boisselle & Sklar, LLP

(57) ABSTRACT

A method for determining a characteristic axis of a body structure includes generating at least two two-dimensional recordings of an area of the body structure; comparing each of the at least two recordings of the area with a generic model of the area in question, said generic model containing information on the position of the characteristic axis; ascertaining a mapping protocol for mapping the respective generic model onto the respective recording of the area; using the ascertained mapping protocol to map the respective position of the characteristic axis in the respective generic model to obtain the respective position of the characteristic axis in the two-dimensional mapping of the body structure; and using rear projection to determine a three-dimensional position of the characteristic axis from the at least two characteristic axes in the two-dimensional mappings.

16 Claims, 4 Drawing Sheets

OTHER PUBLICATIONS

Bras et al. "Personalised 3D reconstruction of proximal femur from low-dose digital biplanar radiographs" International Congress Series 2003.*

Livyatan H. et al., "Gradient-Based 2-D/3-D Rigid Registration of Fluoroscopic X-Ray to CT", IEEE Transactions on Medical Imaging, vol. 22, No. 11, Nov. 2003, pp. 1395-1406, XP-002331109.

Kiss J. et al., "Roentgen Stereophotogrammertric Analysis for Assessing Migration of Total Hip Replacement Femoral Components", Proceedings of the Institution of Mechanical Engineers. Journal of Engineering in Medicine. Part H, Mechanical Engineering Publications Ltd., London, GB, Bd. 209, No. 249, Mar. 1986, pp. 169-175, XP008048138.

Tamaki T. et al., "Femoral Shape Analysis by Bi-Plane X-Ray Photogrammetry", Bulletin of the JSME, Japanese Society of Mechanical Engineers, Tokyo, JP, Bd. 29, No. 249, Mar. 1986, pp. 666-673, XP008048138.

Fleute M. et al., "Nonrigid 3-D/2-D Registration of Images Using Statistical Models", Lecutre Notes in Computer Science, Springer Verlag, New York, NY, Sep. 1999, pp. 138-147, XP008010626.

Browbank I. et al., "Robotic-Assisted Internal Fixation of Hip Fractures: A Fluoroscopy-Based Intraoperative Registration Technique", Proceedings of the Institution of Mechanical Engineers. Journal of Engineering in Medicine. Part H, Mechanical Engineering Publications Ltd., London, GB, Bd. 214, No. Part H02, 2000, pp. 165-179, XP000954513.

Kak et al., "Algorithms for Reconstruction with Nondiffracting Sources", Chapter 3, "Principles of Computerized Tomographic Imaging", IEEE Press, 1988, pp. 49-105.

Steven W. Smith, Ph.D., "The Scientist and Engineer's Guide to Digital Signal Processing", Computed Tomography, http://www.dspguide.com/ch25/5.htm.

* cited by examiner (1) Landmark
(2) Femur reference array
(3) First X-ray projection plane
(4) Second X-ray projection plane
(5) Femur model
(6) C-arm / X-ray device
(7) X-ray calibration/registration device
(8) Femur neck axis
(9) Femur shaft axis
(10) CCD angle
(11) Bone contours
(12) Pointer
(13) Navigation System

US 8,463,004 B2

DETERMINING SHAFT AND FEMUR NECK AXES AND THREE-DIMENSIONAL RECONSTRUCTION

RELATED APPLICATION DATA

This application claims priority of U.S. Provisional Application No. 60/656,953 filed on Feb. 28, 2005, which is incorporated herein by reference in its entirety.

FIELD OF THE INVENTION

The present invention relates to methods and devices for determining characteristic axes of a body structure and, more particularly, for determining the shaft axis and femur neck axis of an upper leg bone or femur, and for individually reconstructing a three-dimensional object from two-dimensional recordings.

BACKGROUND OF THE INVENTION

In operations in the area of the hip and, in particular, for preparing a surgical incision for inserting an artificial hip joint, such as, for example, for determining the size and position of an implant, it is preferable, in addition to determining the position and geometry of the hip, to also determine the position and geometry or dimensions of the femur. In particular, the proximal femur and the femur head are of importance to a surgeon for preparing or planning to insert an artificial joint head. In order to ensure that the artificial hip joint functions correctly and to enable a long service life for the artificial joint, the femoral component of the artificial hip joint should be positioned in the bone structure of the femur in a particular position with respect to the shaft axis and the femur neck axis. In particular, a good fitting of the femur implant in the femur neck and/or in the shaft channel is important for a good load distribution of the implant.

During a surgical incision, a surgeon usually relies on a visual assessment of the exposed bone structure to determine the fitting of the femur implant. However, surgical incisions are increasingly performed in such a way that only the smallest possible areas are cut open, such that it is no longer possible to determine the position of an implant by visual assessment alone. Two-dimensional x-ray images are often used to obtain additional information regarding the desired position of implants relative to the bone. However, a partially grainy, two-dimensional x-ray image only provides a surgeon with a mapping of the body structure in question that is roughly shown by different grey scales. From such images, it is difficult to precisely determine the three-dimensional coordinates for correctly positioning an implant in the bone.

Therefore, computer tomography (CT) recordings of the body structure in question are often generated. However, CT recordings subject the patient to a significantly higher radiation exposure relative to the two-dimensional x-ray recordings mentioned above.

SUMMARY OF THE INVENTION

The present invention provides a method for determining characteristic axes of a body structure, such as for determining the three-dimensional position of the femur neck axis or the shaft axis of the upper leg bone or femur. In accordance with the method, at least one and preferably two or more two-dimensional recordings produced from different directions of each of a first area of the body structure and optionally also a second, different area of the body structure. The recordings, for example, can be two-dimensional x-ray recordings of the areas of the body structure, which can be taken using a C-arm apparatus. The position of a characteristic axis, such as the position of the shaft axis, for example, can be determined automatically, manually or by means of an image processing algorithm. The determination can be based on at least one recording of a first area of the body structure, such as from a recording of the femur shaft, for example, by comparison with a generic model containing information on the position of the characteristic axis. The femur neck axis also can be ascertained as a central axis or as quasi-central between the contours or boundaries of one or more two-dimensional femur neck images of the body structure. An axis of symmetry or an axis near to the axis of symmetry or an approximate axis of symmetry can be determined as a central axis.

If there is only a single two-dimensional recording of the body structure, back-projecting an axis quasi-central between the body or boundary structures or an axis ascertained by comparison with a generic model merely defines a first plane in which the axis in question lies. Thus, further information can be preferably obtained for specifying the spatial position of the respective axis. This can be achieved by means of another two-dimensional x-ray recording of the body structure, such as, for example, of the femur neck from a different direction or at a different angle. This x-ray recording also can be used to determine an axis quasi-central between the contours or an axis ascertained by comparison with a generic model, by which the position of a second plane can be determined by means of back-projection. The intersecting straight line of the back-projection planes ascertained from the first and second recordings defines the spatial position of the axis.

Furthermore, at least one and preferably two or more recordings can be generated from different directions and/or angles of a second area of the body structure, such as of the femur head, for example. A statistical, generic or reference model (which can be provided as a two-dimensional or three-dimensional data set) can be compared with the at least one two-dimensional recording of the second area. The statistical, generic, or reference model can be reshaped until it is quasi-congruent or completely congruent with the at least one recording of the second area of the body structure. Such a method is referred to as "matching". Reference is made to the teachings in this respect of EP 1 348 393 A1, EP 1 348 394 A1 and EP 1 498 851 A1 belonging to the Applicant and to WO 01/22368 A1, the teachings of which are hereby incorporated by reference in their entirety.

If the matching method has been performed, then the mapping or shifting and/or reshaping protocol for mapping the generic model onto the two-dimensional recording of the body structure and/or body structure area is known. When the position of the femur neck axis given in the generic model is mapped using this mapping protocol, the position of the femur neck axis in the two-dimensional recording or in three-dimensional space can be determined. If two or more recordings of the body structure and/or the femur neck have been obtained, then the spatial position of the femur neck axis can be clearly defined.

The position of the shaft axis and, with the aid of a generic model, the position of the femur neck axis can be determined, for example, by back-projection from preferably at least two recordings of the femur neck and the shaft of a femur respectively. The shaft axis and neck axis can be determined by directly calculating a central axis between the contours of the shaft, such that if a body structure (e.g., a femur) connected to markers or a reference star is registered, the spatial position of the femur neck axis and the shaft axis of the femur can be ascertained. A femur implant, for example, can be positioned in the femur or navigated to a corresponding location and aligned or inserted, such that the femur implant is optimally arranged with respect to the shaft axis and the femur neck axis. This can significantly reduce later complications, for example, due to significant strain or wear. Thus, it is no longer necessary to obtain a CT recording.

Although the invention is mostly described on the basis of examining an upper leg bone or femur, one or more characteristic axes of a different body structure, such as the lower leg bone or tibia, or other bones, such as vertebrae or the arm, for example, also can be determined using the herein described method.

An anterior-posterior recording is preferably generated using a C-arm apparatus, for example, wherein the anterior-posterior recording can be used as the at least one two-dimensional recording of the body structure and, in particular, of a femur. This results in a two-dimensional mapping of the contours of the proximal part of the femur or femur head, as shown in FIG. 2. Preferably, a so-called Lauenstein recording is performed as another recording in order to determine the position of the femur neck axis, for example, wherein a recording is produced from the direction indicated by L in FIG. 2.

In the two-dimensional recordings of the body structure, the contours defining characteristic structures or boundaries of the body structure are preferably extracted by means of known edge-detection methods. An exemplary edge detection method uses orthogonal curves as described in Hemant Tagare: "Deformable 2-D Template Matching Using Orthogonal Curves" in IEEE Transactions on Medical Imaging 16(1): 108-117 (1997), or by means of a generic algorithm as described in J. Holland: "Adaption in Natural and Artificial Systems", The University of Michigan Press (1975).

Preferably, the body structure is pre-registered before recording, wherein the body structure also can be roughly aligned or moved into an alignment, for example. This is advantageous for the respective recording, as it enables optimum mapping of contours, structures and/or characteristic features of the body structure or areas of the body structure. The body structure can be pre-registered in a known way, using reference stars attached to the body structure, such as to a bone, for example, or on the basis of landmarks, i.e., characteristic points such as protruding or prominent points on the body structure itself. A center of rotation can be determined kinematically (e.g., by moving a joint in different directions) or individual characteristic points, such as the epicondyles, for example, can be determined using a pointer.

Furthermore, surface points on the body structure can be detected, for example, by means of a known mechanical pointer on which markers are arranged, wherein a tip of the pointer is placed onto one or more surface points on the body structure. Using the pointer, a rough model of the surface of the body structure in question can be produced (which easily enables the body structure to be pre-registered) for generating one or more two-dimensional x-ray recordings.

One or more two-dimensional reference recordings or reference data sets of a reference body structure, generated for example from different directions, can be used as a generic model of the body structure or part of the body structure. The reference data set having the greatest similarity with the two-dimensional mapping or recording of the body structure in question can be initially selected by an algorithm as a generic model for the method. Alternatively, if the recording angle is known for a registered body structure, the two-dimensional mapping generated for a reference model when recording from the same direction or a direction deviating only minimally from this direction can be used.

Alternatively or additionally, a three-dimensional data set, obtained for example by CT recordings of a reference body or reference body structure such as a reference femur, also can be used as the generic model. Two-dimensional mappings can be generated, for example, as so-called DRRs (digital reconstructed radiographs), from such a three-dimensional generic model. DDRs are preferably generated as virtual x-ray images of the generic model from the same direction as the recordings of the body structure, which is possible to a high degree of precision and accuracy if the body structure in question previously was pre-registered (roughly or finely) as described above. These DRRs, used as two-dimensional generic data sets, can be matched to the body structure recordings of a person, as described above, in order to determine the position of one or more characteristic axes, such as the femur neck axis of a femur head, for example.

The aforementioned two-dimensional or three-dimensional generic models or reference data sets contain information on the position or course of characteristic axes, such as the femur neck axis and the shaft axis, for example, in the generic model or data set. After matching the reference data set or sets onto the recordings of the body structure, the course of the matched characteristic axes and therefore the course (i.e., the spatial orientation or alignment) of the characteristic axes in the body structure itself are known.

In addition to the outer contours, back-projecting the recordings A1 and A2 (FIG. 4) also can be performed to ascertain the course of inner contours of the body structure, such as a model of the boundary area of the cortical, for example.

In accordance with another aspect of the invention, there is provided a navigation method for an instrument or an implant, wherein the instrument or the implant is navigated such that it is positioned on or in the body structure, relative to, through or with respect to one or more characteristic axes determined as described above.

Furthermore, the invention provides a computer program which, when loaded onto a computer or running on a computer, can perform a method as described above. The invention further provides a program storage medium or computer program product comprising such a program.

A device in accordance with the invention comprises a recording apparatus for generating two-dimensional mappings of a body structure, such as an x-ray apparatus or a C-arm apparatus, for example. The device can be connected to a computational unit which, for example, can calculate a first axis of a body structure defined as a central axis or an approximated axis of symmetry, such as a shaft axis. Further, the computational unit can obtain reference data or generic data, assigned to the corresponding body structure, from a database. Using the data, the computational unit can perform a matching method (e.g., ascertain a mapping protocol that maps the generic model onto the images or data ascertained by the recording device) so as to obtain the course of the characteristic axis in the recording and, therefore, in the examined body structure. To obtain the course of the characteristic axis in the examined body structure, the computational unit can apply the ascertained mapping protocol to the data on the course of a characteristic axis in the recording, which is contained in the generic model.

The device preferably is connected to a navigation system, such that the data on the spatial course of the characteristic axis of the body structure, as ascertained by the device, can be used by the navigation system. That data can be used to navigate an instrument or implant or to position an instrument or implant at a given location in a defined alignment, for example.

In accordance with another aspect of the invention that can be used independent of or in conjunction with the above-described method, there is provided a method for approximating three-dimensional contour points of an object. The object can be a body structure as described above, wherein at least one two-dimensional projection recording and preferably at least two or more two-dimensional recordings (e.g., x-ray recordings) of the object or body structure from preferably different angles or directions can be used to approximate or determine the three-dimensional contour points or surface points of the object. The two-dimensional outer contours of the mapped object can be initially determined in the projection recordings, wherein the points forming the contour can be referred to as contour points. Furthermore, one or more three-dimensional reference points can be determined, such as estimated mid-points in particular layers of the object. If, for example, three-dimensional contour points or surface points of a cylindrical object are to be determined or approximated, then points along the central axis of the cylindrical object can be advantageously used as three-dimensional reference points. Each three-dimensional reference point thus determined can be projected onto the two-dimensional projection planes of the mapping of the object. At least one and preferably two respective outer contour points in the respective projections can be calculated with respect to the reference point, wherein preferably the reference point should be approximately or exactly the mid-point of the two contour points. The contour points, for example, can be orthogonal to the central axis in the two-dimensional projection.

Determining the mid-point can be optionally refined by calculating the straight line projection for each contour point, such as the straight line g11 in FIG. 4. The angle-bisecting plane, such as w1 and w2 in FIG. 4, can be calculated for each of the pairs of straight line projections defined in the individual recordings, i.e., the angle bisector orthogonal to the plane defined by the two straight line projections. The angle-bisecting planes can be intersected in order to obtain a central line, indicated in FIG. 4 by M. The mid-point then can be calculated as a point of intersection or approximation of the central line vs. the reference plane, reference axis or reference point. The reference plane, for example, can be defined as the plane through the three-dimensional reference point, orthogonal to the three-dimensional central axis as the reference axis.

The three-dimensional contour points can be calculated by dropping the perpendicular from the calculated mid-point onto the straight line projections g11, g12, g21 and g22. The root points of the respective perpendicular, indicated in FIG. 4 by P11, P12, P21, P22, give the approximations of the contour points of the object O. Alternatively, other methods of calculation also can be used in which additional geometric constraints can be taken into account. The distance between the mid-point and the contour, such as for example a radius, can be used as a constraint if it is known.

Optionally, additional points can be calculated, for example on the rear side of the contour. If only two projection recordings of the object are used, the reconstructed points can be predominantly on one side of the object. When generating a three-dimensional shape model from a generic model, this can result in instability, since similar arrangements of three-dimensional points in a relatively narrow range can result in significantly different object sizes. Therefore, an additional geometric orientated reconstruction of points on the rear side of the object can be advantageous. Alternatively, additional recordings also can be acquired, though with ionizing imaging methods, this would increase the radiation exposure for the patient and the operation team.

Points in an extension of the line between the center of projection and a found/estimated mid-point or reference point then can be calculated. The distance value from available information, such as, for example, distances for the three-dimensional contour points already found, can be estimated. In many cases, a cross-determination of the distances is appropriate, wherein the distance for a second recording can be ascertained from the distances between the reference point and edge points from a first recording. This is especially important for elliptical objects, in which the expansion in one direction approximately corresponds to the distances from the mid-point/central line to the contour in the other direction. A three-dimensional structure then can be optionally reconstructed from a generic shape model on the basis of the reconstructed points, such as a statistical shape model, for example, for bone structures.

In the case of cylindrical or quasi-cylindrical objects, such as the shaft axis of a femur, for example, it is advantageous if the recording direction for producing the two-dimensional mappings of the three-dimensional object is approximately orthogonal to the central axis of the object.

An approximating reconstruction of three-dimensional points from two-dimensional projection recordings can be performed by taking geometric constraints into account. This presents the advantage that in many cases geometric constraints enable a shape to be more stringently and robustly detected. Point-recording strategies can be specifically optimized. This can also reduce the radiation exposure for the patient. Geometric reconstruction allows a division between three-dimensional point reconstructing and three-dimensional model generating, i.e., generating the three-dimensional shape from a generic model. This can significantly accelerate three-dimensional model generating, since the three-dimensional information does not have to be compared with two-dimensional information, such as, for example, two-dimensional contour points and/or two-dimensional pixel coordinates/grey values and their straight line projections, within the model generating algorithm. The algorithm can be based wholly on three-dimensional information. Substantially more efficient algorithms are therefore possible.

When reconstructing three-dimensional points, it is assumed in the prior art that the contour points in one recording correspond one-to-one with the contour points in the other image. In some thin structures, such as the upper pubic contour, for example, this assumption is justified and also provides very good results. In other structures, for example round/cylindrical objects, the two-dimensional contour points found do not three-dimensionally correspond if the recordings differ by a sufficiently large angle. However, this difference generally is necessary for an accurate three-dimensional reconstruction.

BRIEF DESCRIPTION OF THE DRAWINGS

The forgoing and other embodiments of the invention are hereinafter discussed with reference to the drawings.

DETAILED DESCRIPTION

Figure 1A:
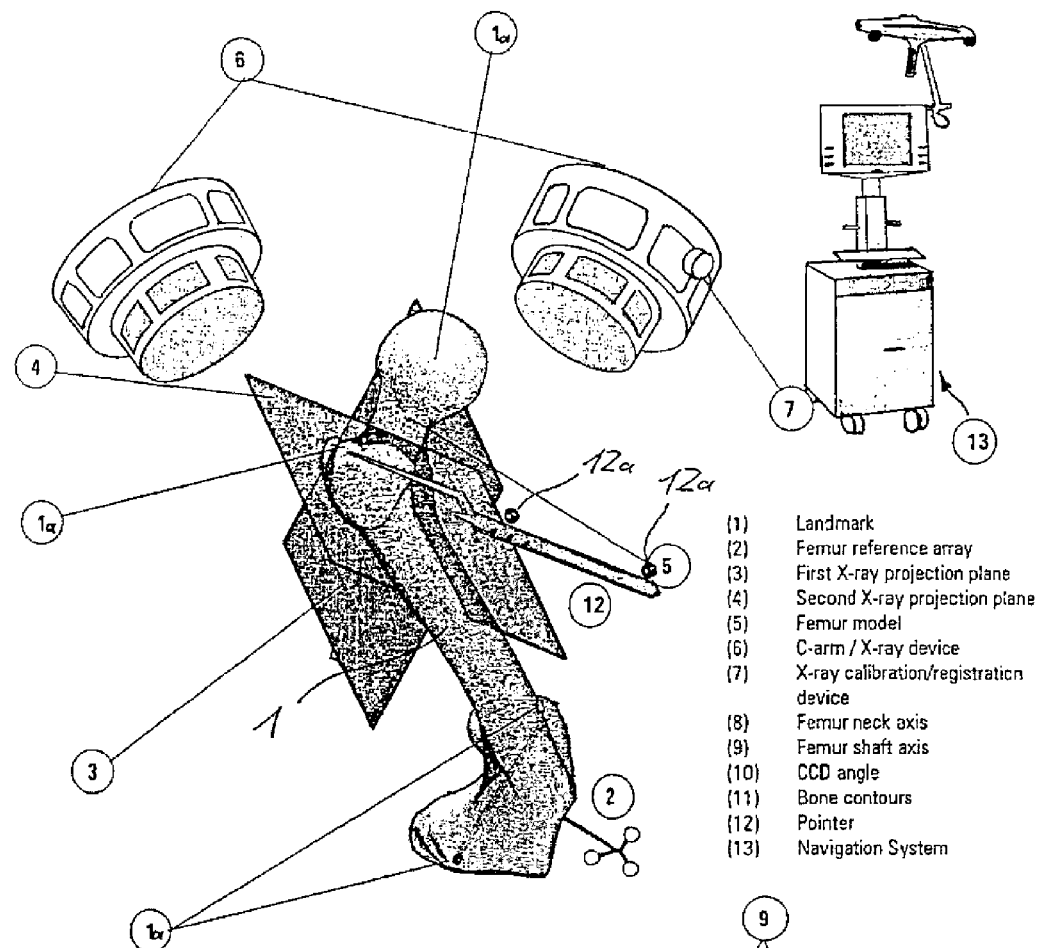
FIGS. 1A-1C illustrate an exemplary device in accordance with the invention.

FIG. 1A shows a femur 1 which exhibits characteristic points or landmarks 1a. A reference star 2 is attached to the femur 1 as a femur reference array. The characteristic points or landmarks 1a on the femur 1 can be detected with the tip of a pointer 12, to which reflective markers 12a are attached. The pointer 12 enables the femur 1 to be at least roughly pre-registered.

Figure 1B:
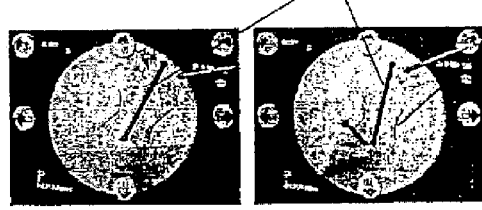
Figure 1C:
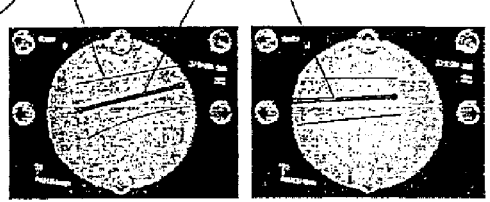

One or more x-ray devices 6, which can be attached to a C-arm and also can comprise markers 7 for calibrating or registering, are used for obtaining recordings. The recordings are generated in a first plane 3 and in a second plane 4 rotated by 90 degrees with respect to the first plane 3, as shown in FIG. 1B for the femur neck and in FIG. 1C for the shaft. The recordings are obtained from two directions offset by 90 degrees with respect to the femur 1. Using the method described above, a computational unit calculates the position of the shaft axis 9 and, after a comparison with a generic model, the position of the femur neck axis 8 is determined.

Figure 2:
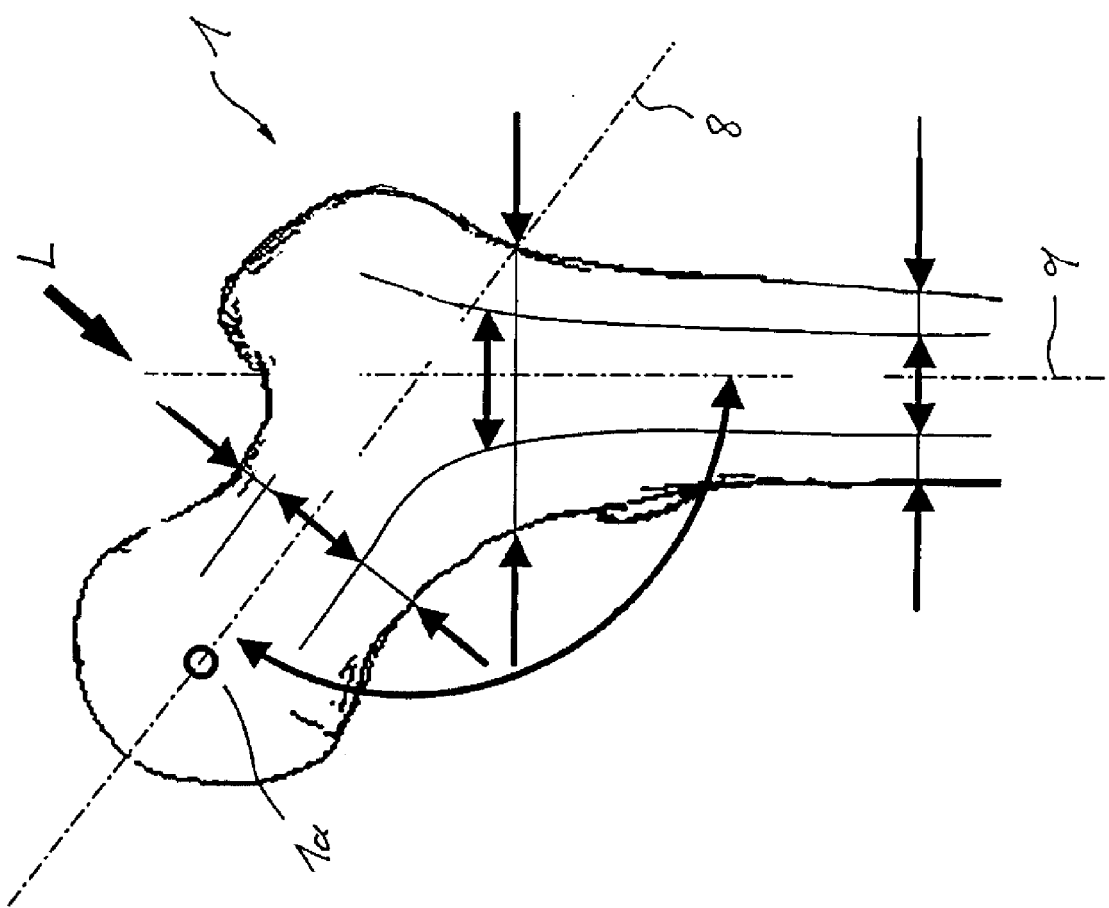
FIG. 2 illustrates an exemplary two-dimensional recording of a femur head in the anterior-posterior direction, which shows the position of the femur neck axis and shaft axis.

FIG. 2 shows a two-dimensional mapping of the femur neck in the first projection plane 3 shown in FIG. 1A. As shown in FIG. 2, the femur neck axis 8 passes through the characteristic point 1a on the femur neck. The anatomical medullary canal runs within the femur 1, wherein the shaft axis 9 is quasi-central to the anatomical medullary canal. The femur neck axis 8 and the shaft axis 9 form the so-called CCD (central column diaphyses) angle. For planning and performing a surgical incision, it is particularly advantageous to know the course of the bone outer contour of the shaft and the femur neck at the proximal femur.

Figure 3:
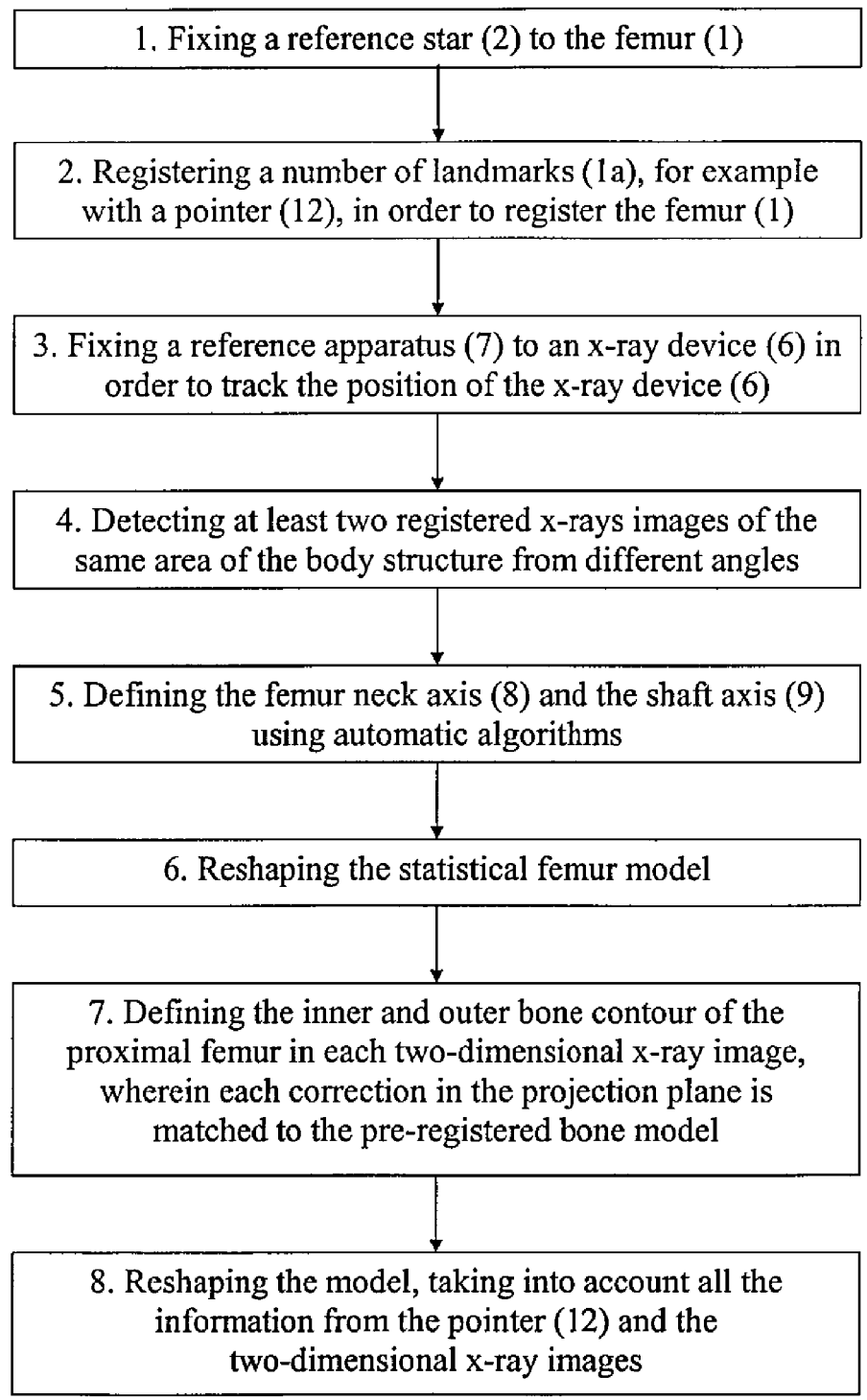
FIG. 3 is a flow diagram for an exemplary method in accordance with the invention.

FIG. 3 shows a flow diagram for performing the method, wherein in Step 1, a reference star 2 is attached to the femur bone 1. A number of landmarks 1a on the femur 1 are then detected, for example with a pointer 12, in order to register the femur 1. A reference star 7, if not already attached, is then fixed to an x-ray apparatus 6 in order to detect the position of the x-ray apparatus relative to the position of the femur 1. This enables assignment of the detected x-ray images to the femur 1 by back-projection.

In step 4, at least two registered x-ray images of one or more areas of interest are recorded from different angles, such as for example two x-ray images of the femur neck and two x-ray images of the shaft of the femur 1. In step 5, the femur neck axes 8 and the shaft axes 9 are then determined in each image, manually or by automatic algorithms, as described above.

Figure 4:
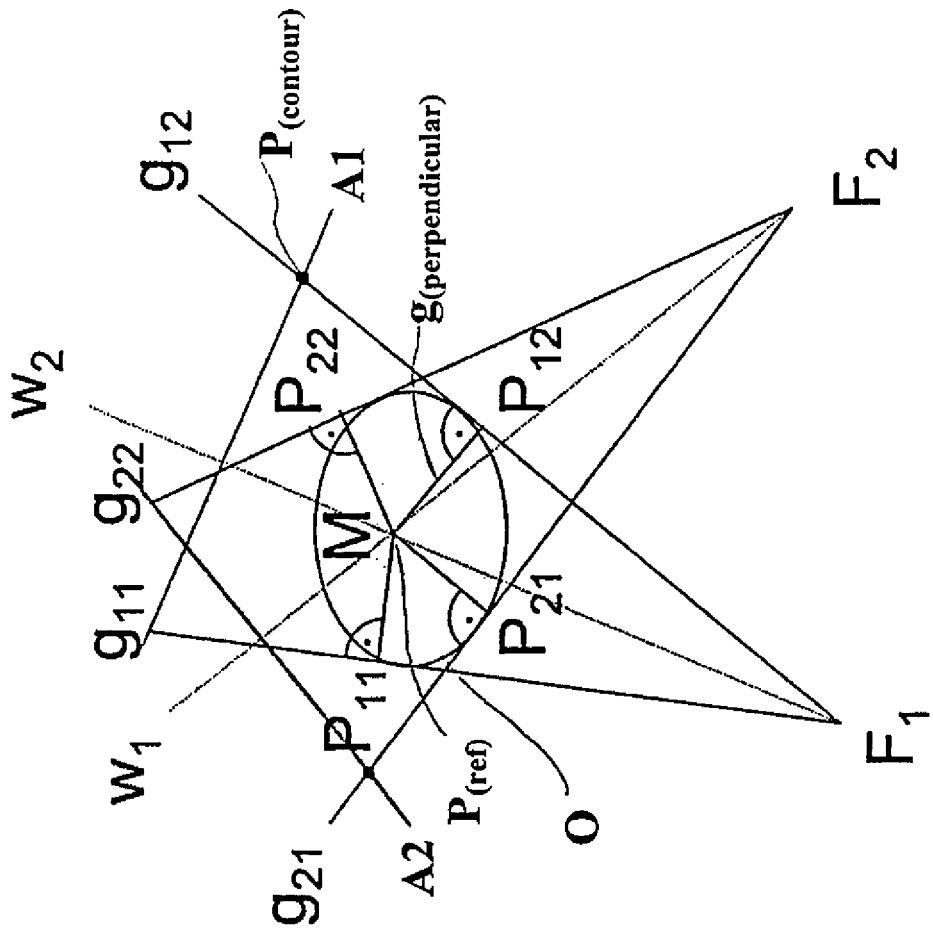
FIG. 4 illustrates a principle for producing an exemplary three-dimensional body structure model from two-dimensional recordings.

A statistical femur model is reshaped in step 6, wherein the back-projection method described on the basis of FIG. 4 can be used to adapt a generic model, or even to produce an approximation model of the contour without using a generic model, by ascertaining a scatterplot of valid three-dimensional points and/or by using layered ellipsoids.

In step 7, the inner and outer bone contour of the proximal femur are then defined in each two-dimensional x-ray image, wherein each contour in the projection plane is matched with the pre-registered bone model or femur model. Next, in step 8 the statistical model is reshaped, taking into account all the information obtained from detecting points using the pointer 12 and from the two-dimensional x-ray images.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining a characteristic axis of a body structure, comprising:
   comparing each of at least two two-dimensional mappings of an area of the body structure with a generic model of the area in question, said generic model containing information on the position of the characteristic axis;
   ascertaining a mapping protocol for mapping the generic model onto the respective mappings of the area;
   using the ascertained mapping protocol to map the position of the characteristic axis in the generic model onto each of the at least two two-dimensional mappings of the area of the body structure; and
   back-projecting the at least two two-dimensional mappings of the area of the body structure to determine a three-dimensional position of the characteristic axis, wherein back-projecting comprises reconstructing, from the at least two two-dimensional mappings, three-dimensional data corresponding to the body structure.

2. The method according to claim 1, further comprising calculating a position of another characteristic axis of the body structure from at least two other two-dimensional mappings of another area, said calculation comprising an intersecting straight line of the back-projection planes of the central axes of the body contours in the two-dimensional mappings.

3. The method according to claim 1, wherein the body structure is a femur, one characteristic axis is the femur neck axis, and the other characteristic axis is the shaft axis.

4. The method according to claim 1, wherein generating two two-dimensional mappings includes generating the mappings from different directions or angles.

5. The method according to claim 1, wherein generating two two-dimensional mappings includes using two-dimensional x-ray images as the mappings.

6. The method according to claim 1, further comprising extracting contours of the body structure.

7. The method according to claim 6, wherein extracting includes using the method of orthogonal curves.

8. The method according to claim 1, further comprising pre-registering the body structure before generating the mappings.

9. The method of claim 8, wherein pre-registering includes using landmarks and/or kinematically ascertained points.

10. The method according to claim 1, wherein the generic model is a data set of two-dimensional mappings of a reference model from different directions.

11. The method according to claim 1, wherein the generic model is a three-dimensional model from which two-dimensional mappings can be obtained.

12. The method according to claim 11, wherein the two-dimensional mappings of the generic model are DDRs.

13. The method according to claim 1, further comprising producing a three-dimensional model of the body structure by back-projecting the two-dimensional mappings, wherein the axes ascertained in the two-dimensional mappings are on the respectively corresponding characteristic axes, and boundary lines or boundary areas of the three-dimensional body structure model are calculated from back-projected body contour mappings.

14. The method according to claim 1, further comprising using an intersecting line of back-projection planes ascertained from back-projecting the at least two two-dimensional mappings of the area to define the three-dimensional position of the characteristic axis.

15. The method according to claim 1, wherein the three-dimensional data corresponds to the at least two two-dimensional mappings.

16. The method according to claim 1, wherein back-projecting comprises smearing each of the at least two two-dimensional mappings back over an image plane to obtain the three-dimensional data.

\* \* \* \* \*